(12) United States Patent
Ito et al.

(10) Patent No.: US 8,334,411 B2
(45) Date of Patent: Dec. 18, 2012

(54) PROCESS FOR PRODUCING DIAMINE AND POLYAMIDE

(75) Inventors: Masateru Ito, Kamakura (JP); Izumi Nakagawa, Kamakura (JP); Koya Kato, Nagoya (JP); Takashi Mimitsuka, Kamakura (JP); Kenji Sawai, Kamakura (JP); Shin-ichi Minegishi, Otsu (JP); Hideki Sawai, Kamakura (JP); Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 262 days.

(21) Appl. No.: 12/920,891

(22) PCT Filed: Mar. 11, 2009

(86) PCT No.: PCT/JP2009/054618
§ 371 (c)(1),
(2), (4) Date: Sep. 20, 2010

(87) PCT Pub. No.: WO2009/113565
PCT Pub. Date: Sep. 17, 2009

(65) Prior Publication Data
US 2011/0004018 A1 Jan. 6, 2011

(30) Foreign Application Priority Data

Mar. 12, 2008 (JP) ................................. 2008-062497
Dec. 17, 2008 (JP) ................................. 2008-321271

(51) Int. Cl.
*C07C 209/84* (2006.01)
*C07C 209/86* (2006.01)
*C07C 231/02* (2006.01)

(52) U.S. Cl. ........ 564/498; 564/138; 564/139; 564/141; 564/159

(58) Field of Classification Search ................... 564/498
See application file for complete search history.

(56) References Cited

U.S. PATENT DOCUMENTS 3,902,967 A 9/1975 Chibata et al.

FOREIGN PATENT DOCUMENTS

| EP | 1 035 212 A2 | 9/2000 |
|---|---|---|
| JP | 49-126891 A | 12/1974 |
| JP | 62-201606 A | 9/1987 |
| JP | 2002-097265 A | 4/2002 |
| JP | 2004-000114 A | 1/2004 |
| JP | 2004-075932 A | 3/2004 |
| JP | 2004-222569 A | 8/2004 |
| JP | 2005-006650 A | 1/2005 |
| JP | 2008-505651 T | 2/2008 |
| WO | 2007/113127 A1 | 10/2007 |

OTHER PUBLICATIONS

Database CAPLUS on STN, Acc. No. 2002:63491, Kato, JP 2002020356 A (Jan. 23, 2002) (abstract).*

* cited by examiner

*Primary Examiner* — Brian J Davis
(74) *Attorney, Agent, or Firm* — DLA Piper LLP (US)

(57) ABSTRACT

A method for producing a diamine includes purifying a diamine from an aqueous solution containing a diamine salt by adding an alkaline substance to the aqueous solution and then filtering the resulting solution by allowing the solution to pass through a nanofiltration membrane to remove the salt, thereby obtaining an aqueous diamine solution.

20 Claims, 1 Drawing Sheet

SEQUENCE LISTING

<160> NUMBER OF SEQ ID NOS: 3

<210> SEQ ID NO 1
<211> LENGTH: 2148
<212> TYPE: DNA
<213> ORGANISM: Escherichia coli

<400> SEQUENCE: 1

```
atgaacgtta ttgcaatatt gaatcacatg ggggtttatt ttaaagaaga acccatccgt      60
gaacttcatc gcgcgcttga acgtctgaac ttccagattg tttacccgaa cgaccgtgac     120
gacttattaa aactgatcga aaacaatgcg cgtctgtgcg gcgttatttt tgactgggat     180
aaatataatc tcgagctgtg cgaagaaatt agcaaaatga cgagaaccct gccgttgtac     240
gcgttcgcta atacgtattc cactctcgat gtaagcctga atgacctgcg tttacagatt     300
agcttctttg aatatgcgct gggtgctgct gaagatattg ctaataagat caagcagacc     360
actgacgaat atatcaacac tattctgcct ccgctgacta agcactgtt taaatatgtt      420
cgtgaaggta aatatacttt ctgtactcct ggtcacatgg cggtactgc attccagaaa       480
agcccggtag gtagcctgtt ctatgatttc tttggtccga ataccatgaa atctgatatt     540
tccatttcag tatctgaact gggttctctg ctggatcaca gtggtccaca caaagaagca     600
gaacagtata tcgctcgcgt cttaacgca gaccgcagct acatggtgac caacggtact       660
tccactgcga acaaaattgt tggtatgtac tctgctccag caggcagcac cattctgatt     720
gaccgtaact gccacaaatc gctgacccac ctgatgatga tgagcgatgt tacgccaatc     780
tatttccgcc cgacccgtaa cgcttacggt attcttggtg gtatcccaca gagtgaattc     840
cagcacgcta ccattgctaa gcgcgtgaaa gaaacaccaa acgcaacctg gccggtacat     900
gctgtaatta ccaactctac ctatgatggt ctgctgtaca acaccgactt catcaagaaa     960
acactggatg tgaaatccat ccactttgac tccgcgtggg tgccttacac caacttctca    1020
ccgatttacg aaggtaaatg cggtatgagc ggtggccgtg tagaagggaa agtgatttac    1080
gaaacccagt ccactcacaa actgctggcg gcgttctctc aggcttccat gatccacgtt    1140
aaaggtgacg taaacgaaga aacctttaac gaagcctaca tgatgcacac caccacttct    1200
ccgcactacg gtatcgtggc gtccactgaa accgctgcgg cgatgatgaa aggcaatgca    1260
ggtaagcgtc tgatcaacgg ttctattgaa cgtgcgatca aattccgtaa agagatcaaa    1320
cgtctgagaa cggaatctga tggctggttc tttgatgtat ggcagccgga tcatatcgat    1380
acgactgaat gctggccgct gcgttctgac agcacctggc acggcttcaa aaacatcgat    1440
aacgagcaca tgtatcttga cccgatcaaa gtcaccctgc tgactccggg gatggaaaaa    1500
gacggcacca tgagcgactt tggtattccg gccagcatcg tggcgaaata cctcgacgaa    1560
catggcatcg ttgttgagaa accggtccg tataacctgc tgttcctgtt cagcatcggt    1620
atcgataaga ccaaagcact gagcctgctg cgtgctctga ctgactttaa acgtgcgttc    1680
gacctgaacc tgcgtgtgaa aaacatgctg ccgtctctgt atcgtgaaga tcctgaattc    1740
tatgaaaaca tgcgtattca ggaactggct cagaatatcc acaaactgat tgttcaccac    1800
aatctgccgg atctgatgta tcgcgcattt gaagtgctgc cgacgatggt aatgactccg    1860
tatgctgcat tccagaaaga gctgcacggt atgaccgaag aagtttacct cgacgaaatg    1920
gtaggtcgta ttaacgccaa tatgatcctt ccgtacccgc cggagttcc tctggtaatg    1980
ccgggtgaaa tgatcaccga agaaagccgt ccggttctgg agttcctgca gatgctgtgt    2040
```

```
gaaatcggcg ctcactatcc gggctttgaa accgatattc acggtgcata ccgtcaggct    2100
gatggccgct ataccgttaa ggtattgaaa gaagaaagca aaaaataa                 2148

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cttcccttgt tctagataat tatttttttgc tttct                              35

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gacccggact caagcttcaa aaatgaaatt aggag                               35
```

PROCESS FOR PRODUCING DIAMINE AND POLYAMIDE

RELATED APPLICATIONS

This is a §371 of International Application No. PCT/JP2009/054618, with an international filing date of Mar. 11, 2009 (WO 2009/113565 A1, published Sep. 17, 2009), which is based on Japanese Patent Application Nos. 2008-062497, filed Mar. 12, 2008, and 2008-321271, filed Dec. 17, 2008, the subject matter of which is incorporated by reference.

SEQUENCE LISTING

The instant application contains a Sequence Listing which has been submitted in ASCII format via EFS-Web and is hereby incorporated by reference in its entirety. Said ASCII copy, created on Sep. 30, 2010, is named TOR10134.txt and is 3,849 bytes in size.

TECHNICAL FIELD

This disclosure relates to a method for producing a diamine comprising the step of purifying a diamine from an aqueous solution containing a diamine salt, and further to a method for producing a polyamide using, as a raw material, a diamine obtained by the method for producing the diamine.

BACKGROUND

As represented by nylons, diamines are used in many fields as raw materials of polyamides. A polyamide is obtained by polyconderisation reaction, under heat condition, of diamine dicarboxylate having a molar ratio between a diamine and a dicarboxylic acid of 1:1. However, since, depending on the diamine as the raw material, the mole balance between the diamine and the dicarboxylic acid may change during the polymerization reaction due to a high volatility of the diamine, the diamine may be required to be added in an excess amount with respect to the dicarboxylic acid (e.g., JP 2004-75932A). Since the diamine to be added must be a highly pure product with which physical properties of the polyamide resin will not be deteriorated, a technology to simply purify a diamine from an aqueous solution containing a diamine salt to obtain a highly pure product has been demanded.

Conventionally, for purification of a diamine from a diamine salt (e.g., diamine sulfate), a method is known wherein an alkaline substance. (e.g., sodium hydroxide) is added to the diamine salt to increase the pH, leading to release of the diamine to produce the free diamine, followed by separation of the salt (e.g., sodium sulfate) produced by the addition of the alkaline substance by an operation such as extraction, and further purification of the free diamine by distillation (see, for example, JP 2004-114 A). However, in cases where a diamine and a salt are separated from each other by an operation such as extraction, a large quantity of an organic solvent (e.g., aniline, chloroform or the like) is required, and in cases where the diamine has a low partition coefficient, the recovery of the diamine in the organic solvent layer is low, so that repeated extraction operations with the organic solvent is necessary, which is problematic. Further, since, after the extraction operation, large quantities of the organic solvent and an aqueous solution containing the organic solvent are discharged, there are problems of increase in the cost of waste disposal and increase in the environmental load.

It could therefore be helpful to attain effective removal of a diamine salt without an extraction operation upon purification of a diamine from the diamine salt, thereby providing a method for efficiently purifying a diamine suitable as a raw material for a polyamide.

SUMMARY

We discovered that filtration of an aqueous solution containing a diamine salt using a nanofiltration membrane enables highly efficient removal of the salt in the aqueous solution. We thus provide:

[1] A method for producing a diamine comprising the step of purifying a diamine from an aqueous solution containing a diamine salt, the method comprising the step of adding an alkaline substance to the aqueous solution and then filtering the resulting solution by allowing the solution to pass through a nanofiltration membrane to remove the salt, thereby obtaining an aqueous diamine solution.

[2] The method for producing a diamine according to [1], wherein the diamine salt is a salt of a diamine represented by Chemical Formula (1):

$$H_2N-(CH_2)_n-NH_2 \quad (1)$$

wherein n represents an integer of 1 to 10.

[3] The method for producing a diamine according to [1] or [2], wherein the diamine salt is a diamine inorganic acid salt or a diamine dicarboxylate.

[4] The method for producing a diamine according to any one of [1] to [3], wherein the alkaline substance is sodium hydroxide, potassium hydroxide, calcium hydroxide or ammonia.

[5] The method for producing a diamine according to any one of [1] to [4], wherein a functional layer of the nanofiltration membrane comprises a polyamide.

[6] The method for producing a diamine according to [5], wherein the polyamide comprises a cross-linked piperazine polyamide as a major component and a constituting component represented by Chemical Formula (2):

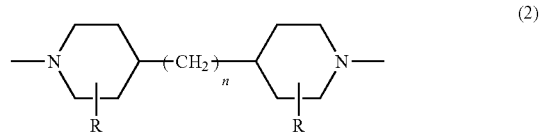

(2)

wherein R represents —H or —CH₃, and n represents an integer of 0 to 3.

[7] The method for producing a diamine according to any one of [1] to [6], wherein the aqueous solution after the addition of the alkaline substance in the step has a pH of not less than 9 and not more than 12.

[8] The method for producing a diamine according to any one of [1] to [7], wherein the filtration pressure of the aqueous solution in the step is not less than 0.1 MPa and not more than 8 MPa.

[9] The method for producing a diamine according to any one of [1] to [8], wherein the aqueous diamine solution obtained by the step is further subjected to a step of distillation under a pressure of not less than 1 Pa and not more than atmospheric pressure, at a temperature of not less than 25° C. and not more than 200° C.

[10] The method for producing a diamine according to any one of [1] to [9], wherein the aqueous diamine solution obtained by the step is further subjected to a step of filtering through a reverse osmosis membrane to increase the diamine concentration.

[11] A method for producing a polyamide comprising the step of polycondensation of the diamine obtained by the method for producing a diamine according to any one of [1] to [10] with a dicarboxylic acid.

[12] A method for producing a polyamide according to [11], wherein the dicarboxylic acid is adipic acid.

By our method for producing a diamine, a salt contained in an aqueous diamine salt solution can be effectively removed by an operation simpler than the conventional extraction operation with an organic solvent, so that a diamine suitable as a raw material of a polyamide can be obtained.

DESCRIPTION OF SYMBOLS

Figure 1:
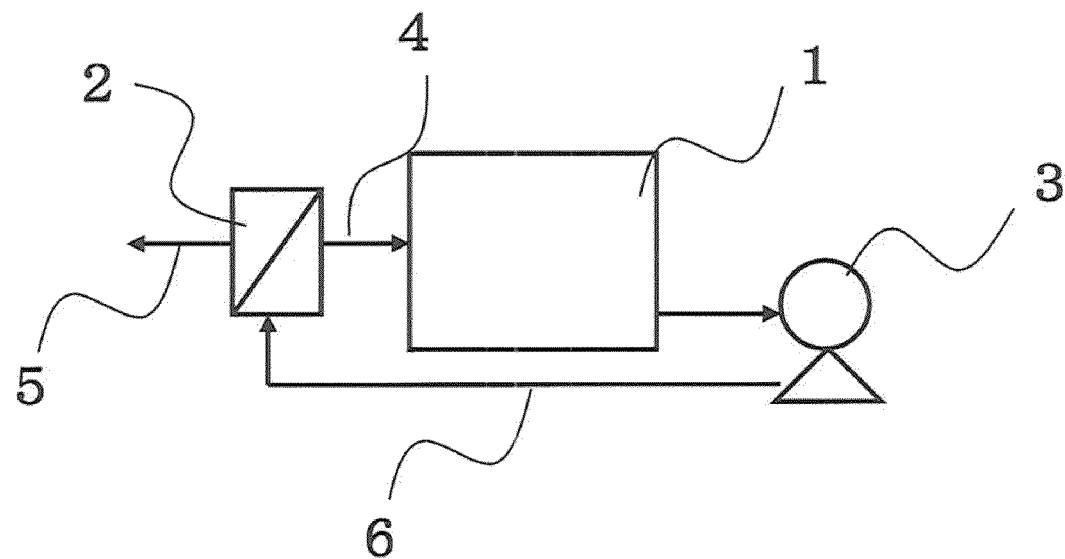
FIG. 1 is a schematic diagram showing a nanofiltration membrane separation device.

1. Raw solution tank
2. Cell in which a nanofiltration membrane is placed
3. High-pressure pump
4. Flow of a membrane-concentrated solution
5. Flow of a membrane-permeated solution
6. Flow of the culture sent from the high-pressure pump
7. Nanofiltration membrane
8. Supporting plate

DETAILED DESCRIPTION

Our methods will now be described in more detail.

The method for producing a diamine comprises a step wherein an alkaline substance is added to an aqueous solution containing a diamine salt and the resulting solution is filtered by being allowed to pass through a nanofiltration membrane to remove the salt, thereby obtaining an aqueous diamine solution.

The nanofiltration membrane used in the method for producing a diamine is also called a nanofiltration membrane or an NF membrane, and is a membrane generally defined as "membrane permeating a monovalent ion but preventing a divalent ion." It is a membrane probably having a fine pore of about several nanometers, and it is mainly used to prevent fine particles, molecules, ions, salts and the like in water. The nanofiltration membrane preferably allows permeation of monovalent ions but blocks divalent ions.

Examples of the material of the nanofiltration membrane which may be used include polymer materials such as cellulose acetate-based polymers, polyamides, polyesters, polyimides and vinyl polymers. The membrane is not restricted to a membrane constituted by a single type of the material but may also be a membrane comprising a plurality of membrane materials. In terms of the membrane structure, the membrane may be either an asymmetric membrane having a dense layer on at least one side of the membrane, wherein the pore size of each micropore gradually increases in the direction from the dense layer to the inside of the membrane or the other side thereof; or a composite membrane having a very thin functional layer formed by another material on the dense layer of an asymmetric membrane. Examples of the composite membrane which may be used include a composite membrane wherein a nanofiltration membrane having a polyamide functional layer is constituted on a supporting membrane comprising a polysulfone as a membrane material, as described in JP 62-201606 A.

Among these, a composite membrane comprising a polyamide as a functional layer is preferred which has a high pressure resistance, a high permeability and a high solute-removing performance and an excellent potential. Further, to be capable of maintaining a high durability against the operation pressure, a high permeability and a high rejection performance, a composite membrane having a structure in which a polyamide constitutes a functional layer and the layer is retained by a support comprising a porous membrane or a non-woven fabric is preferred. As the nanofiltration membrane comprising a polyamide as a functional layer, a composite nanofiltration membrane comprising as a support a functional layer comprising a cross-linked polyamide obtained by polycondensation reaction of a multifunctional amine with a multifunctional acid halide is preferred.

In the nanofiltration membrane containing a polyamide as a functional layer, preferred examples of the monomer carboxylic acid component constituting the polyamide include aromatic carboxylic acids such as trimesic acid, benzophenone tetracarboxylic acid, trimellitic acid, pyromellitic acid, isophthalic acid, terephthalic acid, naphthalenedicarboxylic acid, biphenylcarboxylic acid and pyridinecarboxylic acid, and in view of solubility to film-forming solvents, trimesic acid, isophthalic acid and terephthalic acid and mixtures thereof are more preferred.

Preferred examples of amine component of the monomer constituting the polyamide include primary diamines having an aromatic ring(s) such as m-phenylenediamine, p-phenylene-diamine, benzidine, methylenebisdianiline, 4,4'-diaminobiphenylether, dianisidine, 3,3',4-triaminobiphenylether, 3,3',4,4'-tetraaminobiphenylether, 3,3'-dioxybenzidine, 1,8-naphthalenediamine, m(p)-monomethylphenylenediamine, 3,3'-monomethylamino-4,4'-diaminobiphenylether, 4,N,N'-(4-aminobenzoyl)-p(m)-phenylenediamine-2,2'-bis(4-aminophenylbenzoimidazole), zole), 2,2'-bis(4-aminophenylbenzooxazole) and 2,2'-bis(4-aminophenylbenzothiazole); and secondary diamines such as piperazine, piperidine and derivatives thereof, and among these, a nanofiltration membrane having a functional layer comprising a cross-linked polyamide containing piperazine or piperidine as a monomer is preferably used because of not only its pressure resistance and durability, but also its heat resistance and chemical resistance. More preferably, the polyamide comprises the cross-linked piperazine polyamide or the cross-linked piperidine polyamide as a major component and, further contains the constituting component represented by the above Chemical Formula (2), and still more preferably, the polyamide comprises the cross-linked piperazine polyamide as a major component and further contains a constituting component represented by the above Chemical Formula (2). Among the constituting components represented by the above Chemical Formula (2), those wherein n=3 are preferably used. Examples of the nanofiltration membrane which has a functional layer comprising a cross-linked piperadine polyamide as a major component and further contains a constituting component represented by the above Chemical Formula (2) include one described in JP 62-201606 A, and particular examples thereof include UTC 60, which is a cross-linked piperadine-based polyamide nanofiltration membrane manufactured by Toray Industries, Inc. having a functional layer which comprises a cross-linked piperadine polyamide as a major component and further contains a constituting component represented by the above Chemical Formula (2) wherein n=3.

A nanofiltration membrane is generally used as a spiral-type membrane element. The nanofiltration membrane is also preferably used, and can also be applied, as a spiral-type membrane element. Preferred particular examples of the nanofiltration membrane which may be used include. SU-210, SU-220, SU-600 and SU-610, which are nanofiltration modules manufactured by Toray Industries, Inc. including UTC60 manufactured by the same company. Additional examples include NF-45, NF-90, NF-200 and NF-400, which are nanofiltration membranes manufactured by FilmTec Corporation having a functional layer comprising a cross-linked piperazine-based polyamide; NF99, NF97 and NF99HF, which are nanofiltration membranes manufactured by Alfa Laval having a functional layer comprising a polyamide; and GEsepa, which is a cellulose acetate nanofiltration membrane manufactured by GE Osmonics.

The term "allow to pass through a nanofiltration membrane" in the method for producing a diamine means a process wherein an alkaline substance is added to an aqueous solution containing a diamine salt, and the resulting aqueous solution is allowed to pass through a nanofiltration membrane, followed by removing, rejecting or filtering the salt dissolved, or precipitated as solids, in the non-permeated solution side, while allowing an aqueous diamine solution to permeate as a filtrate to the permeated-solution side.

Examples of the method to evaluate the permeability of the nanofiltration membrane to the aqueous diamine solution include a method wherein the diamine permeability is calculated for the evaluation. The diamine permeability can be calculated according to Equation 1 by measuring the concentration of the diamine contained in the raw solution (aqueous solution containing the diamine) (raw solution diamine concentration) and the concentration of the diamine contained in the permeated solution (aqueous diamine solution) (permeated solution diamine concentration) by an analysis represented by high-performance liquid chromatography and gas chromatography:

Diamine permeability (%)=(permeated solution diamine concentration/raw solution diamine concentration)×100          (Equation 1).

In terms of the method for evaluation of the permeation flow rate per unit membrane area per unit pressure (membrane permeation flux), the rate can be calculated according to Equation 2 by measuring the amount of the permeated solution collected, the length of time of the collection of the permeated solution, and the membrane area:

Membrane permeation flux ($m^3/m^2 \cdot day$))=amount of permeated solution/(membrane area×solution collection time)          (Equation 2).

The filtration of the aqueous solution containing a diamine salt by the nanofiltration membrane can be carried out under pressure. The filtration pressure employed is preferably not less than 0.1 MPa and not more than 8 MPa since the membrane permeation rate decreases at a filtration pressure of less than 0.1 MPa, and a filtration pressure of more than 8 MPa affects the membrane to cause damage thereto. In cases where the membrane is used at not less than 0.5 MPa and not more than 7 MPa, the membrane permeation flux is high, so the aqueous diamine solution can be allowed to permeate efficiently and there is less possibility that the filtration pressure affects the membrane to cause damage thereto. Usage of the membrane at not less than 1 MPa and not more than 6 MPa is especially preferred.

During the filtration of the aqueous solution containing a diamine salt through a nanofiltration membrane, the recovery of the permeated solution can be improved by returning the non-permeated solution to the raw solution and repeating filtration of the non-permeated solution. The recovery of the diamine can be calculated according to Equation 3 by measuring the total amount of the diamine before the nanofiltration and the total amount of the diamine which was permeated through the nanofiltration membrane:

Recovery of diamine(%)=(total amount of diamine permeated through nanofiltration membrane/ total amount of diamine before nanofiltration)× 100          (Equation 3).

The nanofiltration membrane used for producing a diamine preferably has a membrane separation performance with which the salt removal rate is not less than 45% when it is evaluated at a temperature of 25° C. in an aqueous sodium chloride solution (500 mg/L) whose pH was adjusted to 6.5, under a filtration pressure of 0.75 MPa. The salt removal rate can be calculated according to Equation 4 by measuring the permeated solution salt concentration in the aqueous sodium chloride solution:

Salt rejection rate=100×{1−(salt concentration in permeated solution/salt concentration in supplied solution)}          (Equation 4).

The nanofiltration membrane applied preferably has a permeation performance with which the membrane permeation flux ($m^3/(m^2 \cdot day)$) is not less than 0.3 for sodium chloride (500 mg/L) under a filtration pressure of 0.3 MPa.

The method for producing a diamine is characterized in that an alkaline substance is added to the aqueous solution containing a diamine salt which is to be allowed to pass through the nanofiltration membrane. At this time, the pH of the aqueous solution containing a diamine salt is preferably not less than 9 and not more than 12. Nanofiltration membranes are more likely to allow permeation of unionized (undissociated) substances in a solution than ionized (dissociated) substances, and therefore, by setting the pH of the aqueous solution containing a diamine salt to not less than 9, the ratio of the unionized diamine in the aqueous solution containing a diamine salt becomes higher than that of the ionized diamine (undissociated diamine/dissociated diamine>1), so that the aqueous diamine solution can be efficiently recovered from the permeated-solution side. In cases where the pH of the aqueous solution containing a diamine salt exceeds 12, the durability of the nanofiltration membrane may be adversely affected.

Examples of the diamine salt provided for the nanofiltration membrane include diamine inorganic acid salts and diamine organic acid salts. Examples of the diamine inorganic acid salts include diamine sulfate, diamine hydrochloride, diamine carbonate, diamine phosphate and diamine nitrate. Examples of the diamine organic acid salts include diamine aliphatic mono-carboxylates (particular examples thereof include diamine formate, diamine acetate, diamine propionate, diamine butyrate, diamine valerate and diamine lactate) and diamine aromatic monocarboxylates (particular examples thereof include diamine benzoate, diamine salicylate, diamine cinnamate and diamine gallate) which are diamine monocarboxylates; diamine aliphatic dicarboxylates (particular examples thereof include diamine oxalate, diamine malonate, diamine malate, diamine fumarate, diamine maleate, diamine glutarate, diamine pimelate, diamine suberate, diamine azelate, diamine sebacate, diamine succinate and diamine adipate) and diamine aromatic dicarboxylates (particular examples thereof include diamine phthalate, diamine isophthalate and diamine terephthalate) which are diamine dicarboxylates; and diamine aliphatic tricarboxylates (particular examples thereof include diamine citrate and diamine aconitate). Diamine dicarboxylates are preferred, and diamine aliphatic dicarboxylates are more preferred.

Examples of the alkaline substance to be added to the aqueous solution containing a diamine salt include lithium hydroxide, sodium hydroxide, potassium hydroxide, calcium hydroxide, magnesium hydroxide, aluminum hydroxide and solids, solutions and gases of ammonia, and among these, addition of sodium hydroxide, potassium hydroxide, calcium hydroxide or ammonia is preferred. In cases where the diamine salt is diamine sulfate, addition of calcium hydroxide as the alkaline substance allows precipitation of insoluble calcium sulfate, which can be filtered with qualitative filter paper or the like as solids, which is more preferred. The concentration of the alkaline substance to be added is not restricted and may exceed the saturation solubility, and the substance may be added in the form of a slurry.

The diamine forming the diamine salt is not restricted, and examples thereof include linear, branched and cyclic aliphatic diamines such as methylenediamine, 1,2-ethylenediamine, 1,3-propanediamine, 1,4-butanediamine, 1,5-pentanediamine, 1,6-hexanediamine, 1,7-heptanediamine, 1,8-octanediamine, 1,9-nonanediamine, 1,10-decanediamine, 1,2-propanediamine and 1,2-butanediamine and 1,2-cyclohexyldiamino; aromatic diamines such as o-phenylenediamine (o-phenyldiamine), m-phenylenediamine (m-phenyldiamine), p-phenylenediamine (p-phenyldiamine) and 1,8-naphthalenediamine; and diamines wherein aliphatic and aromatic diamines are linked to each other. The diamine forming the diamine salt may also be a diamine wherein carboxylic acid is linked, such as lysine. Preferred examples of the diamine include aliphatic diamines represented by the Chemical Formula (1) (particular examples thereof include methylenediamine, 1,2-ethylenediamine, 1,3-propanediamine, 1,4-butanediamine, 1,5-pentanediamine, 1,6-hexanediamine, 1,7-heptanediamine, 1,8-octanediamine, 1,9-nonanediamine and 1,10-decanediamine), and the diamine is more preferably a diamine wherein, in Chemical Formula (1), n represents 1 to 6 (particular examples thereof include methylenediamine, 1,2-ethylenediamine, 1,3-propanediamine, 1,4-butanediamine, 1,5-pentanediamine or 1,6-hexanediamine), still more preferably 1,5-pentanediamine which corresponds to Chemical Formula (1) in which n=5. The diamine purified is not restricted to a single type, and a mixture of a plurality of types of diamines can also be preferably purified.

The method for producing the diamine salt is not restricted, and examples of the production method include the organic synthesis method, fermentation method, enzyme method and resting microorganism method. In the cases of the fermentation method and the enzyme method, a culture containing a diamine salt is also included in the aqueous diamine salt solution of the present invention. More specifically, in cases where the diamine to be purified is 1,5-pentanediamine, 1,5-pentanediamine is purified from, for example, an aqueous 1,5-pentanediamine salt solution produced by the lysine decarboxylase reaction in the enzyme method described in JP 2004-114 A or JP 2005-6650 A using lysine as the raw material, or an aqueous solution or a culture containing a 1,5-pentanediamine salt obtained by the fermentation method described in JP 2004-222569 A or WO 2007/113127 using sugars as the raw materials. In cases where the diamine to be purified is 1,4-butanediamine, 1,4-butanediamine can be purified from a culture containing a 1,4-butanediamine salt obtained by the ornithine decarboxylase reaction described in Japanese Translated PCT Patent Application Laid-open No. 2008-505651 using ornithine as the raw material. In cases where the diamine to be purified is L-lysine, L-lysine can be purified from, for example, a culture containing an L-lysine salt obtained by the fermentation method described in JP 49-126891 A using sugars as the raw materials.

The concentration of the diamine salt in the aqueous diamine salt solution used in the method for producing a diamine is not restricted, and a higher concentration enables reduction of the time needed for concentrating the aqueous diamine solution which has permeated the nanofiltration membrane, which is preferred in view of reduction of the cost. The concentration is preferably not less than 5 g/L and not more than 200 g/L.

Preferably, the separation membrane device having the nanofiltration membrane will now be described. The separation membrane device having the nanofiltration membrane may be constituted by mainly a raw solution tank to store the culture and a cell in which a high-pressure pump to provide the driving force for the filtration and a cell of nanofiltration membrane are placed.

Figure 2:
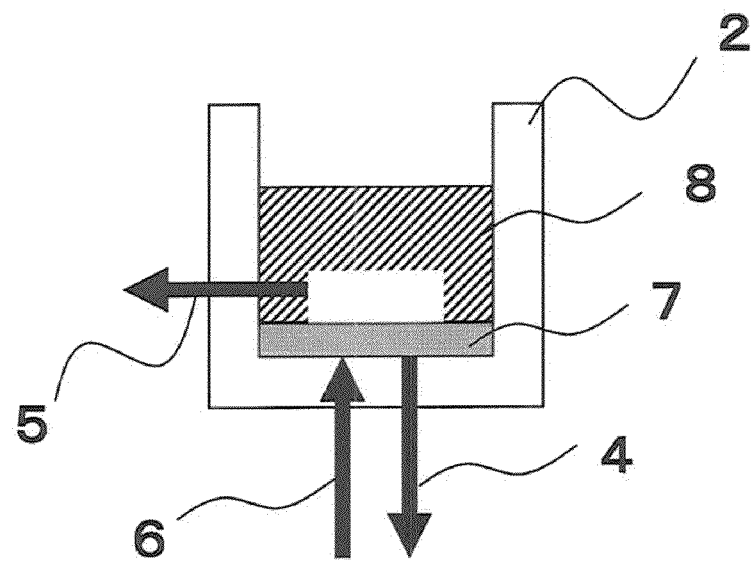
FIG. 2 is a schematic diagram showing a cross-sectional view of a cell in which the nanofiltration membrane of the nanofiltration membrane separation device is placed.

FIG. 1 is a schematic diagram to explain an example of the separation membrane device having the nanofiltration membrane which may be used. FIG. 2 is a schematic cross-sectional view of the cell to explain an example of the separation membrane device having the nanofiltration membrane in which the nanofiltration membrane is placed. An example of the purification of a diamine by the separation membrane device having the nanofiltration membrane in FIG. 1 will now be described. The nanofiltration membrane 7 is placed in the cell 2 using a supporting plate 8. Subsequently, an aqueous diamine salt solution is fed to the raw solution tank, and the aqueous diamine salt solution is then sent to the cell by the high-pressure pump 3, to purify the diamine. The filtration pressure by the high-pressure pump 3 may be not less than 0.1 MPa and not more than 8 MPa. The filtration pressure is preferably not less than 0.5 MPa and not more than 7 MPa, and especially preferably not less than 1 MPa and not more than 6 MPa. The aqueous diamine salt solution is sent to the cell 2 to obtain a permeated solution 5 which contains the purified diamine. The concentrated solution 4 which was yielded by concentration in the cell is again returned to the raw solution tank 1. At this time, the purification of the diamine can also be carried out continuously by feeding an additional diamine salt to the raw solution tank in the same amount as the permeated solution (not shown in the figure). Thus, a diamine, which is the desired product, and impurities in an aqueous diarnine salt solution can be separated from each other to simply purify the diamine.

The filtration step by a nanofiltration membrane may be combined with another diamine purification step, and a highly pure diamine can be obtained by obtaining an aqueous diamine solution by filtration through the nanofiltration membrane followed by subjecting the resulting aqueous diamine solution to a step of distillation. The step of distillation is carried out preferably under a reduced pressure of not less than 1 Pa and not more than atmospheric pressure (normal pressure; about 101 kPa), more preferably under a reduced pressure of not less than 100 Pa and not more than 15 kPa. In cases where the distillation is carried out under reduced pressure, the distillation temperature is preferably not less than 20° C. and not more than 200° C., more preferably not less than 50° C. and not more than 180° C. Before subjecting to the step of distillation, the aqueous diamine solution that has permeated through the nanofiltration membrane may once be concentrated using a concentration device represented by an evaporator.

Further, a process wherein the aqueous diamine solution obtained by filtration through the nanofiltration membrane is further subjected to a step of filtration through a reverse osmosis membrane to increase the diamine concentration in the aqueous solution may be preferably applied. The reverse osmosis membrane is a filtration membrane for removal of ions and low-molecular-weight molecules using a pressure difference higher than the osmotic pressure of the solution to be processed. Examples of the reverse osmosis membrane which may be used in the process include those of the cellulose-based type such as ones based on cellulose acetate, and membranes wherein a polyamide separation functional layer is provided on a microporous supporting membrane by polycondensation of a multifunctional amine compound and a multifunctional acid halide. For example, to suppress dirt on the surface of the reverse osmosis membrane, that is, fouling, a low-fouling reverse osmosis membrane for mainly sewage treatment may also be preferably used, wherein the surface of a polyamide separation functional layer was covered with an aqueous solution of a compound having at least one reactive group which reacts with an acid halide group, to allow formation of a covalent bond(s) between the acid halide group remaining on the surface of the separation functional layer and the reactive group(s). Since the salt can be mostly removed by the nanofiltration, membrane concentration can be stably carried out without forming scales on the surface of the reverse osmosis membrane.

Particular examples of the reverse osmosis membrane include SU-710, SU-720, SU-720F, SU-710L, SU-720L, SU-720LF, SU-720R, SU-710P and SU-720P, which are low-pressure type polyamide-based reverse osmosis membrane modules manufactured by Toray Industries, Inc., and SU-810, SU-820, SU-820L and SU-820FA, which are high-pressure type modules having UTC70 as the reverse osmosis membrane; SC-L100R, SC-L200R, SC-1100, SC-1200, SC-2100, SC-2200, SC-3100, SC-3200, SC-8100 and SC-8200, which are cellulose acetate-based reverse osmosis membranes manufactured by the same company; NTR-759HR, NTR-729HF, NTR-70SWC, ES10-D, ES20-D, ES20-U, ES15-D, ES15-U and LF10-D manufactured by Nino Denko Corporation; RO98pHt, R099, HR98PP and CE4040C-30D manufactured by Alfa-Laval; GE Sepa manufactured by GE; BW30-4040, TW30-4040, XLE-4040, LP-4040, LE-4040, SW30-4040 and SW3OHRLE-4040 manufactured by Filmtec.

The filtration by the reverse osmosis membrane is carried out under pressure, and the filtration pressure is preferably within the range of not less than 1 MPa and not more than 8 MPa, since a filtration pressure of less than 1 MPa leads to decrease in the membrane permeation rate, and a filtration pressure of not less than 8 MPa affects the membrane to cause damage thereto. In cases where the filtration pressure is within the range, of not less than 1 MPa and not more than 7 MPa, the membrane permeation flux is high, so the aqueous diamine solution can be efficiently concentrated. The filtration pressure is most preferably within the range of not less than 2 MPa and not more than 6 MPa since there is less possibility that the filtration pressure affects the membrane to cause damage thereto in this case.

The diamine obtained by the method can be used as a raw material for a polyamide. As the method for producing a polyamide using the diamine as a raw material, a known method wherein a diamine is subjected to polycondensation with a dicarboxylic acid can be applied (see Osamu Fukumoto ed. "Polyamide Resin Handbook", The Nikkan Kogyo Shimbun, Ltd. (January, 1998); or JP 2004-75932 A).

Examples of the dicarboxylic acid which can be subjected to the polycondensation with a diamine include aliphatic dicarboxylic acids such as oxalic acid, malonic acid, malic acid, fumaric acid, maleic acid, glutaric acid, pimelic acid, suberic acid, azelaic acid, sebacic acid, dodecanedioic acid, succinic acid and adipic acid; and aromatic dicarboxylic acids such as phthalic acid, isophthalic acid and terephthalic acid, and among these, aliphatic dicarboxylic acids are preferred, and adipic acid is more preferred.

Examples of the polyamide obtained by the method for producing a polyamide include polyhexamethylene adipamide (nylon 66) in the case of polycondensation between hexamethylenediamine and adipic acid; polyhexamethylene sebacamide (nylon 610) in the case of polycondensation between hexamethylenediamine and sebacic acid; polyhexamethylene terephthalamide (nylon 6T) in the case of polycondensation between hexamethylenediamine and terephthalic acid; polyhexamethylene isophthalamide (nylon 6I) in the case of polycondensation between hexamethylenediamine and isophthalic acid; polypentamethylene adipamide (nylon 56) in the case of polycondensation between 1,5-pentanediamine and adipic acid; and polypentamethylene sebacamide (nylon 510) in the case of polycondensation between 1,5-pentanediamine and sebacic acid; and copolymers thereof such as a copolymer between nylon 6T and nylon 66 (nylon 6T/66) and a copolymer between nylon 6T and nylon 6I (nylon 6T/6I).

The polymerization degree of the polyamide obtained by the method for producing a polyamide is not restricted, and the relative viscosity $\eta r$ is preferably 1.5 to 8.0, more preferably 2.0 to 7.0 when measurement was carried out in 98% sulfuric acid at a concentration of 0.01 g/mL at 25° C. using an Ostwald viscometer.

Examples

Our methods will now be described in more detail, but this disclosure is not restricted to the Examples below.

Preparation of the Nanofiltration Membrane

As the nanofiltration membrane, each of a cross-linked piperazine polyamide-based nanofiltration membrane "UTC60" (nanofiltration membrane 1; manufactured by Toray Industries, Inc.), a cross-linked piperazine polyamide-based "NF-400" (nanofiltration membrane 2; manufactured by FilmTec), a polyamide-based nanofiltration membrane "NF99" (nanofiltration membrane 3; manufactured by Alfa Laval) and a cellulose acetate-based nanofiltration membrane "GEsepa" (nanofiltration membrane 4; manufactured by GE Osmonics) was placed in a stainless (SUS316) cell as shown in FIG. 2.

The Method for Analysis of the Diamirie Concentration by HPLC

Column used: CAPCELL PAK C18 (Shiseido)
Mobile phase: 0.1% (w/w) $H_3PO_4$:acetonitrile=4.5:5.5
Detection: UV 360 nm
Pretreatment of samples: To 25 µl of each sample to be analyzed, 25 µl of 1,3-propanediamine (0.03 M) as an internal standard, 150 µl of sodium hydrogen carbonate (0.075 M) and a 2,4-dinitrofluorobenzene solution in ethanol (0.2 M) were added, and the resulting mixture was mixed, followed by incubation at 37° C. for 1 hour. In 1 ml of acetonetrile, 50 µl of the above reaction solution was dissolved, and the resulting solution was centrifuged at 10000 rpm for 5 minutes, followed by analyzing a 10 µl aliquot of the resultant by HPLC.

Preparation of the Diamine Salt

A 10 g/L aqueous solution (50 L) of each of 1,4-butanediamine (manufactured by Wako Pure Chemicals), 1,5-pentanediamine (manufactured by Wako Pure Chemicals) and 1,6-hexanediamine (manufactured by Wako Pure Chemicals) was prepared, and concentrated sulfuric acid (manufactured by Wako Pure Chemicals) was added to the solution to pH 7, to obtain each diamine sulfate as the starting material for Examples 1 to 9.

Examples 1 to 12

Preparation of an Aqueous 1,4-Butanediamine Sulfate Solution to be Subjected to Separation by the Nanofiltration Membrane To the 10 g/L aqueous 1,4-butanediamine sulfate solution (50 L), 1 M aqueous calcium hydroxide solution (manufactured by Wako Pure Chemicals) was added to pH 9, 10 and 11, respectively, followed by stirring the resulting solution for 1 hour at 25° C. The precipitated calcium sulfate was filtered by suction filtration using qualitative filter paper No. 2 (manufactured by Advantec), thereby collecting 50 L of the filtrate.

Separation Experiment by the Nanofiltration Membrane

Subsequently, 50 L of the filtrate obtained as above was injected to the raw solution tank 1 of the membrane filtration device as shown in FIG. 1, and the pressure by the high-pressure pump 3 was adjusted to 1 MPa to allow the filtrate to pass through the nanofiltration membrane, thereby collecting the permeated solution 5. The concentrations of sulfate ion and calcium ion contained in the raw solution tank 1 and the permeated solution 5 were analyzed by an ion chromatography (manufactured by DIONEX), and the concentration of 1,4-butanediamine was analyzed by a high-performance liquid chromatography (manufactured by Shimadzu Corporation). The results are shown in Table 1.

As shown in Table 1, it can be seen that, by the nanofiltration membrane, calcium sulfate was removed at a high efficiency and 1,4-butanediamine was recovered at a high yield at any of the pHs of 9, 10 and 11.

Examples 13 to 24

Preparation of an Aqueous 1,5-Pentanediamine Sulfate Solution to be Subjected to Separation by the Nanofiltration Membrane To the 10 g/L aqueous 1,5-pentanediamine sulfate solution (50 L), 1 M aqueous calcium hydroxide solution (manufactured by Wako Pure Chemicals) was added to pH 9, 10 and 11, respectively, followed by stirring the resulting solution for 1 hour at 25° C. The precipitated calcium sulfate was filtered by suction filtration using qualitative filter paper No. 2 (manufactured by Advantec), thereby collecting 50 L of the filtrate.

Separation Experiment by the Nanofiltration Membrane

Subsequently, 50 L of the filtrate obtained as above was injected to the raw solution tank 1 of the membrane filtration device as shown in FIG. 1, and the pressure by the high-pressure pump 3 was adjusted to 1 MPa to allow the filtrate to pass through the nanofiltration membrane, thereby collecting the permeated solution 5. The concentrations of sulfate ion and calcium ion contained in the raw solution tank 1 and the permeated solution 5 were analyzed by an ion chromatography (manufactured by DIONEX), and the concentration of 1,5-pentanediamine was analyzed by a high-performance liquid chromatography (manufactured by Shimadzu Corporation). The results are shown in Table 2.

TABLE 1

| | | | Calcium ion concentration | | | Sulfate ion concentration | | | 1,4-Butanediamine concentration | | | |
|---|---|---|---|---|---|---|---|---|---|---|---|---|
| | | pH | Raw solution (mg/L) | Permeated solution (mg/L) | Rejection rate (%) | Raw solution (mg/L) | Permeated solution (mg/L) | Rejection rate (%) | Raw solution (g/L) | Permeated solution (g/L) | Permeation rate (%) | 1,4-Butanediamine recovery (%) |
| Example 1 | Nanofiltration membrane 1 | 9 | 576 | 1 | 99.8 | 1622 | 312 | 80.8 | 10 | 5.8 | 58 | 98.9 |
| Example 2 | Nanofiltration membrane 1 | 10 | 560 | 0.8 | 99.9 | 1754 | 322 | 81.6 | 10 | 6 | 60 | 99 |
| Example 3 | Nanofiltration membrane 1 | 11 | 570 | 0.9 | 99.8 | 1767 | 324 | 81.7 | 10 | 6.2 | 62 | 99.5 |
| Example 4 | Nanofiltration membrane 2 | 9 | 576 | 5.6 | 99.0 | 1622 | 334 | 79.4 | 10 | 5.8 | 58 | 98.4 |
| Example 5 | Nanofiltration membrane 2 | 10 | 560 | 6.1 | 98.9 | 1754 | 349 | 80.1 | 10 | 5.9 | 59 | 98 |
| Example 6 | Nanofiltration membrane 2 | 11 | 570 | 6 | 98.9 | 1767 | 347 | 80.4 | 10 | 6 | 60 | 98.2 |
| Example 7 | Nanofiltration membrane 3 | 9 | 576 | 6.3 | 98.9 | 1622 | 331 | 79.6 | 10 | 5.6 | 56 | 97 |
| Example 8 | Nanofiltration membrane 3 | 10 | 560 | 6.2 | 98.9 | 1754 | 332 | 81.1 | 10 | 5.6 | 56 | 97.1 |
| Example 9 | Nanofiltration membrane 3 | 11 | 570 | 6.5 | 98.9 | 1767 | 329 | 81.4 | 10 | 5.9 | 59 | 98.2 |
| Example 10 | Nanofiltration membrane 4 | 9 | 576 | 6.9 | 98.8 | 1622 | 340 | 79.0 | 10 | 4.6 | 46 | 95.5 |
| Example 11 | Nanofiltration membrane 4 | 10 | 560 | 6.7 | 98.8 | 1754 | 349 | 80.1 | 10 | 4.8 | 48 | 94.3 |
| Example 12 | Nanofiltration membrane 4 | 11 | 570 | 6.5 | 98.9 | 1767 | 344 | 80.5 | 10 | 4.8 | 48 | 94 |

TABLE 2

| | | pH | Calcium ion concentration Raw solution (mg/L) | Calcium ion concentration Permeated solution (mg/L) | Calcium ion concentration Rejection rate (%) | Sulfate ion concentration Raw solution (mg/L) | Sulfate ion concentration Permeated solution (mg/L) | Sulfate ion concentration Rejection rate (%) | 1,5-Pentanediamine concentration Raw solution (g/L) | 1,5-Pentanediamine concentration Permeated solution (g/L) | Permeation rate (%) | 1,5-Pentanediamine recovery (%) |
|---|---|---|---|---|---|---|---|---|---|---|---|---|
| Example 13 | Nanofiltration membrane 1 | 9 | 588 | 1.2 | 99.8 | 1710 | 331 | 80.6 | 10 | 5.3 | 53 | 98.1 |
| Example 14 | Nanofiltration membrane 1 | 10 | 561 | 0.8 | 99.9 | 1698 | 314 | 81.5 | 10 | 5.6 | 56 | 98.5 |
| Example 15 | Nanofiltration membrane 1 | 11 | 577 | 0.8 | 99.9 | 1677 | 331 | 80.3 | 10 | 5.8 | 58 | 99.6 |
| Example 16 | Nanofiltration membrane 2 | 9 | 588 | 5.6 | 99.0 | 1710 | 354 | 79.3 | 10 | 5.2 | 52 | 98 |
| Example 17 | Nanofiltration membrane 2 | 10 | 561 | 6 | 98.9 | 1698 | 334 | 80.3 | 10 | 5.2 | 52 | 97.7 |
| Example 18 | Nanofiltration membrane 2 | 11 | 577 | 6.6 | 98.9 | 1677 | 331 | 80.3 | 10 | 5.5 | 55 | 97.9 |
| Example 19 | Nanofiltration membrane 3 | 9 | 588 | 6.4 | 98.9 | 1710 | 312 | 81.8 | 10 | 5.1 | 51 | 98.6 |
| Example 20 | Nanofiltration membrane 3 | 10 | 561 | 6.4 | 98.9 | 1698 | 311 | 81.7 | 10 | 5.2 | 52 | 98.1 |
| Example 21 | Nanofiltration membrane 3 | 11 | 577 | 6.5 | 98.9 | 1677 | 315 | 81.2 | 10 | 5.1 | 51 | 98.1 |
| Example 22 | Nanofiltration membrane 4 | 9 | 588 | 7 | 98.8 | 1710 | 332 | 80.6 | 10 | 4.4 | 44 | 95.1 |
| Example 23 | Nanofiltration membrane 4 | 10 | 561 | 6.9 | 98.8 | 1698 | 335 | 80.3 | 10 | 4.5 | 45 | 94.3 |
| Example 24 | Nanofiltration membrane 4 | 11 | 577 | 6.9 | 98.8 | 1677 | 333 | 80.1 | 10 | 4.5 | 45 | 94.2 |

As shown in Table 2, it can be seen that, by the nanofiltration membrane, calcium sulfate was removed at a high efficiency and 1,5-pentanediamine was recovered at a high yield at any of the pHs of 9, 10 and 11.

Examples 25 to 36

Preparation of an Aqueous 1,6-Hexanediamine Sulfate Solution to be Subjected to Separation by the Nanofiltration Membrane To the 10 g/L aqueous 1,6-hexanediamine sulfate solution (50 L), 1 M aqueous calcium hydroxide solution was added to pH 9, 10 and 11, respectively, followed by stirring the resulting solution for 1 hour at 25° C. The precipitated calcium sulfate was filtered by suction filtration using qualitative filter paper No. 2 (manufactured by Advantec), thereby collecting 50 L of the filtrate.

Separation Experiment by the Nanofiltration Membrane

Subsequently, 50 L of the filtrate obtained as above was injected to the raw solution tank 1 of the membrane filtration device as shown in FIG. 1, and the pressure by the high-pressure pump 3 was adjusted to 1 MPa to allow the filtrate to pass through the nanofiltration membrane, thereby collecting the permeated solution 5. The concentrations of sulfate ion and calcium ion contained in the raw solution tank 1 and the permeated solution 5 were analyzed by an ion chromatography (manufactured by DIONEX), and the concentration of 1,6-hexanediamine was analyzed by a high-performance liquid chromatography (manufactured by Shimadzu Corporation). The results are shown in Table 3.

TABLE 3

| | | pH | Calcium ion concentration Raw solution (mg/L) | Calcium ion concentration Permeated solution (mg/L) | Calcium ion concentration Rejection rate (%) | Sulfate ion concentration Raw solution (mg/L) | Sulfate ion concentration Permeated solution (mg/L) | Sulfate ion concentration Rejection rate (%) | 1,6-Hexanediamine concentration Raw solution (g/L) | 1,6-Hexanediamine concentration Permeated solution (g/L) | Permeation rate (%) | 1,6-Hexanediamine recovery (%) |
|---|---|---|---|---|---|---|---|---|---|---|---|---|
| Example 25 | Nanofiltration membrane 1 | 9 | 589 | 1 | 99.8 | 1659 | 319 | 80.8 | 10 | 4.8 | 48 | 97.9 |
| Example 26 | Nanofiltration membrane 1 | 10 | 579 | 0.8 | 99.9 | 1670 | 320 | 80.8 | 10 | 5 | 50 | 98.4 |
| Example 27 | Nanofiltration membrane 1 | 11 | 576 | 0.8 | 99.9 | 1711 | 341 | 80.1 | 10 | 5.1 | 51 | 98.9 |
| Example 28 | Nanofiltration membrane 2 | 9 | 589 | 5.4 | 99.1 | 1659 | 349 | 79.0 | 10 | 4.6 | 46 | 97.7 |
| Example 29 | Nanofiltration membrane 2 | 10 | 579 | 5.6 | 99.0 | 1670 | 325 | 80.5 | 10 | 4.8 | 48 | 98 |
| Example 30 | Nanofiltration membrane 2 | 11 | 576 | 6.3 | 98.9 | 1711 | 333 | 80.5 | 10 | 5.1 | 51 | 98.1 |
| Example 31 | Nanofiltration membrane 3 | 9 | 589 | 6.7 | 98.9 | 1659 | 313 | 81.1 | 10 | 4.7 | 47 | 97.8 |
| Example 32 | Nanofiltration membrane 3 | 10 | 579 | 7 | 98.8 | 1670 | 332 | 80.1 | 10 | 4.9 | 49 | 98.4 |

TABLE 3-continued

| | | pH | Calcium ion concentration | | | Sulfate ion concentration | | | 1,6-Hexanediamine concentration | | | 1,6-Hexanediamine recovery (%) |
|---|---|---|---|---|---|---|---|---|---|---|---|---|
| | | | Raw solution (mg/L) | Permeated solution (mg/L) | Rejection rate (%) | Raw solution (mg/L) | Permeated solution (mg/L) | Rejection rate (%) | Raw solution (g/L) | Permeated solution (g/L) | Permeation rate (%) | |
| Example 33 | Nanofiltration membrane 3 | 11 | 576 | 7 | 98.8 | 1711 | 311 | 81.8 | 10 | 5 | 50 | 98.4 |
| Example 34 | Nanofiltration membrane 4 | 9 | 589 | 6.9 | 98.8 | 1659 | 301 | 81.9 | 10 | 3.5 | 35 | 93 |
| Example 35 | Nanofiltration membrane 4 | 10 | 579 | 6.9 | 98.8 | 1670 | 302 | 81.9 | 10 | 3.5 | 35 | 93.3 |
| Example 36 | Nanofiltration membrane 4 | 11 | 576 | 6.9 | 98.8 | 1711 | 301 | 82.4 | 10 | 3.6 | 56 | 93.5 |

As shown in Table 3, it can be seen that, by the nanofiltration membrane, calcium sulfate was removed at a high efficiency and 1,6-hexanediamine was recovered at a high yield at any of the pHs of 9, 10 and 11.

Examples 37 to 48

Preparation of an Aqueous 1,5-Pentanediamine Adipate Solution to be Subjected to Separation by the Nanofiltration Membrane To 10 g/L 1,5-pentanediamine (manufactured by Wako Pure Chemicals), 10 g/L aqueous adipic acid solution (manufactured by Wako Pure Chemicals) was added to pH 7, to provide an aqueous 1,5-pentanediamine adipate solution (50 L). To the resulting solution, 1 M aqueous calcium hydroxide solution (manufactured by Wako Pure Chemicals) was added to pH 9, 10 and 11, respectively, followed by stirring the resulting solution for 1 hour at 25° C.

Separation Experiment by the Nanofiltration Membrane

Subsequently, 50 L of the aqueous solution obtained as above was injected to the raw solution tank 1 of the membrane filtration device as shown in FIG. 1, and the pressure by the high-pressure pump 3 was adjusted to 1 MPa to allow the filtrate to pass through the nanofiltration membrane, thereby collecting the permeated solution 5. The concentration of calcium ion contained in the raw solution tank 1 and the permeated solution 5 was analyzed by an ion chromatography (manufactured by DIONEX), and the concentrations of 1,5-pentanediamine and adipic acid were analyzed by a high-performance liquid chromatography (manufactured by Shimadzu Corporation). The results are shown in Table 4.

TABLE 4

| | | pH | Calcium ion concentration | | | Adipic acid concentration | | | 1,5-Pentanediamine concentration | | | 1,5-Pentanediamine recovery (%) |
|---|---|---|---|---|---|---|---|---|---|---|---|---|
| | | | Raw solution (mg/L) | Permeated solution (mg/L) | Rejection rate (%) | Raw solution (mg/L) | Permeated solution (mg/L) | Rejection rate (%) | Raw solution (g/L) | Permeated solution (g/L) | Permeation rate (%) | |
| Example 37 | Nanofiltration membrane 1 | 9 | 589 | 1.1 | 99.8 | 1669 | 317 | 81.0 | 10 | 5.3 | 53 | 98.4 |
| Example 38 | Nanofiltration membrane 1 | 10 | 588 | 0.8 | 99.9 | 1701 | 322 | 81.1 | 10 | 5.5 | 55 | 98.6 |
| Example 39 | Nanofiltration membrane 1 | 11 | 580 | 0.7 | 99.9 | 1721 | 341 | 80.2 | 10 | 5.9 | 59 | 99 |
| Example 40 | Nanofiltration membrane 2 | 9 | 589 | 5.4 | 99.1 | 1669 | 323 | 80.6 | 10 | 5 | 50 | 97.5 |
| Example 41 | Nanofiltration membrane 2 | 10 | 588 | 5.5 | 99.1 | 1701 | 323 | 81.0 | 10 | 5.1 | 51 | 97.8 |
| Example 42 | Nanofiltration membrane 2 | 11 | 580 | 5.7 | 99.0 | 1721 | 340 | 80.2 | 10 | 5.4 | 54 | 97.7 |
| Example 43 | Nanofiltration membrane 3 | 9 | 589 | 6.3 | 98.9 | 1669 | 330 | 80.2 | 10 | 5.1 | 51 | 97.6 |
| Example 44 | Nanofiltration membrane 3 | 10 | 588 | 6.4 | 98.9 | 1701 | 324 | 81.0 | 10 | 5.2 | 52 | 98.1 |
| Example 45 | Nanofiltration membrane 3 | 11 | 580 | 6.3 | 98.9 | 1721 | 337 | 80.4 | 10 | 5.4 | 54 | 98.3 |
| Example 46 | Nanofiltration membrane 4 | 9 | 589 | 6.9 | 98.8 | 1669 | 308 | 81.5 | 10 | 4.5 | 45 | 94.4 |
| Example 47 | Nanofiltration membrane 4 | 10 | 588 | 6.8 | 98.8 | 1701 | 312 | 81.7 | 10 | 4.6 | 46 | 94.6 |
| Example 48 | Nanofiltration membrane 4 | 11 | 580 | 6.8 | 98.8 | 1721 | 311 | 81.9 | 10 | 4.7 | 47 | 94.6 |

As shown in Table 4, it can be seen that, by the nanofiltration membrane, calcium adipate was removed at a high efficiency and 1,5-pentanediamine was recovered at a high yield at any of the pHs of 9, 10 and 11.

Each of the above Example 1 to Example 48 was carried out using a single nanofiltration membrane, without replacing the membrane to a new one. In spite of this, under the above filtration pressure, calcium sulfate could be removed highly efficiently.

Examples 49 to 60

Preparation of 1,5-Pentanediamine Sulfate Produced by the Enzyme Method

First, L-lysine decarboxylase was prepared according to the method described in Reference Example 1(1) to (3) in JP 2004-114 A. Subsequently, aqueous 50% L-lysine solution (manufactured by Fluka) was diluted to obtain aqueous 20% solution, and sulfuric acid was added dropwise to the aqueous solution to pH 6, to prepare an aqueous lysine sulfate solution. To the above aqueous lysine sulfate solution, pyridoxal phosphate monohydrate having a final concentration of 0.05 mM (manufactured by Fluka) was added, and L-lysine decarboxylase having a final concentration of 50 mg/L was added to the resulting solution. The resulting mixture was allowed to react at 45° C. for 48 hours. After the reaction, the prepared aqueous 1,5-pentanediamine sulfate solution was diluted to prepare 10 g/L aqueous 1,5-pentanediamine sulfate solution (50 L).

Preparation of an Aqueous 1,5-Pentanediamine Sulfate Solution to be Subjected to Separation by the Nanofiltration Membrane To the aqueous 10 g/L 1,5-pentanediamine sulfate solution (50 L), 1 M aqueous calcium hydroxide solution (manufactured by Wako Pure Chemicals) was added to pH 9, 10 and 11, respectively, followed by stirring the resulting solution for 1 hour at 25° C. The precipitated calcium sulfate was filtered by suction filtration using qualitative filter paper No. 2 (manufactured by Advantec), thereby collecting 50 L of the filtrate.

Separation Experiment by the Nanofiltration Membrane

Subsequently, 50 L of the aqueous solution obtained as above was injected to the raw solution tank 1 of the membrane filtration device as shown in FIG. 1, and the pressure by the high-pressure pump 3 was adjusted to 1 MPa to allow the filtrate to pass through the nanofiltration membrane, thereby collecting the permeated solution 5. The concentrations of sulfate ion and calcium ion contained in the raw solution tank 1 and the permeated solution 5 were analyzed by an ion chromatography (manufactured by DIONEX), and the concentration of 1,5-pentanediamine was analyzed by a high-performance liquid chromatography (manufactured by Shimadzu Corporation). The results are shown in Table 5.

TABLE 5

| | | pH | Calcium ion concentration | | | Sulfate ion concentration | | | 1,5-Pentanediamine concentration | | | 1,5-Pentanediamine recovery (%) |
| | | | Raw solution (mg/L) | Permeated solution (mg/L) | Rejection rate (%) | Raw solution (mg/L) | Permeated solution (mg/L) | Rejection rate (%) | Raw solution (g/L) | Permeated solution (g/L) | Permeation rate (%) | |
| --- | --- | --- | --- | --- | --- | --- | --- | --- | --- | --- | --- | --- |
| Example 49 | Nanofiltration membrane 1 | 9 | 598 | 1.2 | 99.8 | 1723 | 331 | 80.8 | 10 | 5.4 | 54 | 98 |
| Example 50 | Nanofiltration membrane 1 | 10 | 580 | 0.8 | 99.9 | 1701 | 314 | 81.5 | 10 | 5.5 | 55 | 98.3 |
| Example 51 | Nanofiltration membrane 1 | 11 | 587 | 0.8 | 99.9 | 1733 | 331 | 80.9 | 10 | 5.9 | 59 | 99.4 |
| Example 52 | Nanofiltration membrane 2 | 9 | 598 | 5.6 | 99.1 | 1723 | 350 | 79.7 | 10 | 5.2 | 52 | 97.5 |
| Example 53 | Nanofiltration membrane 2 | 10 | 580 | 6.1 | 98.9 | 1701 | 344 | 79.8 | 10 | 5.2 | 52 | 97.6 |
| Example 54 | Nanofiltration membrane 2 | 11 | 587 | 6.5 | 98.9 | 1733 | 333 | 80.8 | 10 | 5.4 | 54 | 97.5 |
| Example 55 | Nanofiltration membrane 3 | 9 | 598 | 6.3 | 98.9 | 1723 | 316 | 81.7 | 10 | 5 | 50 | 97.5 |
| Example 56 | Nanofiltration membrane 3 | 10 | 580 | 6.4 | 98.9 | 1701 | 315 | 81.5 | 10 | 5.1 | 51 | 97.6 |
| Example 57 | Nanofiltration membrane 3 | 11 | 587 | 6.6 | 98.9 | 1733 | 315 | 81.8 | 10 | 5.2 | 52 | 97.9 |
| Example 58 | Nanofiltration membrane 4 | 9 | 598 | 6.9 | 98.8 | 1723 | 313 | 81.8 | 10 | 4.5 | 45 | 94.1 |
| Example 59 | Nanofiltration membrane 4 | 10 | 580 | 7 | 98.8 | 1701 | 314 | 81.5 | 10 | 4.6 | 46 | 94.4 |
| Example 60 | Nanofiltration membrane 4 | 11 | 587 | 7 | 98.8 | 1733 | 331 | 80.9 | 10 | 4.6 | 46 | 94.9 |

As shown in Table 5, it can be seen that, by the nanofiltration membrane, calcium sulfate was removed at a high efficiency and 1,5-pentanediamine was recovered at a high yield at any of the pHs of 9, 10 and 11.

Examples 61 to 72

Preparation of 1,5-Pentanediamine Adipate Produced by the Enzyme Method

First, L-lysine decarboxylase was prepared according to the method described in Reference Example 1(1) to (3) in JP 2004-114 A. Subsequently, aqueous 50% L-lysine solution (manufactured by Fluka) was diluted to obtain aqueous 20% solution, and adipic acid (manufactured by Wako Pure Chemicals) was added dropwise to the aqueous solution to pH 6, to prepare an aqueous lysine sulfate solution. To the above aqueous lysine adipate solution, pyridoxal phosphate monohydrate (manufactured by Fluka) was added to a final concentration of 0.05 mM, and L-lysine decarboxylase was added to the resulting solution to a final concentration of 50 mg/L. The resulting mixture was allowed to react at 45° C. for 48 hours. After the reaction, the prepared aqueous 1,5-pentanediamine adipate solution was diluted to prepare 10 g/L aqueous 1,5-pentanediamine adipate solution (50 L).

Preparation of an Aqueous 1,5-Pentanediamine Adipate Solution to be Subjected to Separation by the Nanofiltration Membrane To the 10 g/L aqueous 1,5-pentanediamine adipate solution (50 L), 1 M aqueous calcium hydroxide solution (manufactured by Wako Pure Chemicals) was added to pH 9, 10 and 11, respectively, followed by stirring the resulting solution for 1 hour at 25° C. The precipitated calcium adipate was filtered by suction filtration using qualitative filter paper No. 2 (manufactured by Advantec), thereby collecting 50 L of the filtrate.

Separation Experiment by the Nanofiltration Membrane

Subsequently, 50 L of the aqueous solution obtained as above was injected to the raw solution tank 1 of the membrane filtration device as shown in FIG. 1, and the pressure by the high-pressure pump 3 was adjusted to 1 MPa to allow the filtrate to pass through the nanofiltration membrane, thereby collecting the permeated solution 5. The concentrations of calcium ion contained in the raw solution tank 1 and the permeated solution 5 were analyzed by an ion chromatography (manufactured by DIONEX), and the concentrations of 1,5-pentanediamine and adipic acid were analyzed by a high-performance liquid chromatography (manufactured by Shimadzu. Corporation). The results are shown in Table 6.

As shown in Table 6, it can be seen that, by the nanofiltration membrane, calcium adipate was removed at a high efficiency and 1,5-pentanediamine was recovered at a high yield at any of the pHs of 9, 10 and 11.

Examples 73 to 84

Preparation of 1,5-Pentanediamine Sulfate Produced by the Fermentation Method (1) Preparation of a Vector Which Expresses Lysine Decarboxylase Based on the base sequence of the lysine decarboxylase gene in *E. coli* (SEQ ID NO:1) registered in a database (GenBank), PCR primers (SEQ ID NOs:2 and 3) were designed. At the ends of the PCR primers, a HindIII restriction site and an XbaI restriction site were added, respectively.

Using these primers, PCR was carried out using the genomic DNA of the *E. coli* K12 strain (ATCC 10798) as the template, to obtain an amplified fragment of about 2.2 kb. This amplified fragment was digested with HindIII and XbaI (TAKARA BIO) and then introduced to the HindIII/XbaI-restriction site in pUC19 (TAKARA BIO), to prepare the lysine decarboxylase expression vector pCAD1. In pCADA, the cadA gene was introduced in the downstream of the lac promoter, so that induction of expression is possible with IPTG.

(2) Introduction of the Expression Vector to a Host

The expression vector pCAD1 prepared in (1) was introduced to the *E. coli* JM109 strain. After the introduction, selection of recombinant *E. coli* was carried out using as an index the resistance to an antibiotic ampicillin, thereby obtaining a transformant. This transformant was designated the *E. coli* CAD1 strain.

TABLE 6

| | | | Calcium ion concentration | | | Adipic acid concentration | | | 1,5-Pentanediamine concentration | | | |
|---|---|---|---|---|---|---|---|---|---|---|---|---|
| | | pH | Raw solution (mg/L) | Permeated solution (mg/L) | Rejection rate (%) | Raw solution (mg/L) | Permeated solution (mg/L) | Rejection rate (%) | Raw solution (g/L) | Permeated solution (g/L) | Permeation rate (%) | 1,5-Pentanediamine recovery (%) |
| Example 61 | Nanofiltration membrane 1 | 9 | 589 | 1.1 | 99.8 | 1669 | 317 | 81.0 | 10 | 5.3 | 53 | 98.4 |
| Example 62 | Nanofiltration membrane 1 | 10 | 588 | 0.8 | 99.9 | 1701 | 322 | 81.1 | 10 | 5.5 | 55 | 98.6 |
| Example 63 | Nanofiltration membrane 1 | 11 | 580 | 0.7 | 99.9 | 1721 | 341 | 80.2 | 10 | 5.9 | 59 | 99 |
| Example 64 | Nanofiltration membrane 2 | 9 | 589 | 5.5 | 99.1 | 1669 | 321 | 80.8 | 10 | 5 | 50 | 97.5 |
| Example 65 | Nanofiltration membrane 2 | 10 | 588 | 5.5 | 99.1 | 1701 | 323 | 81.0 | 10 | 5.3 | 53 | 97.6 |
| Example 66 | Nanofiltration membrane 2 | 11 | 580 | 5.7 | 99.0 | 1721 | 333 | 80.7 | 10 | 5.4 | 54 | 97.7 |
| Example 67 | Nanofiltration membrane 3 | 9 | 589 | 6 | 99.0 | 1669 | 321 | 80.8 | 10 | 5.1 | 51 | 97.4 |
| Example 68 | Nanofiltration membrane 3 | 10 | 588 | 6.5 | 98.9 | 1701 | 322 | 81.1 | 10 | 5.3 | 53 | 97.5 |
| Example 69 | Nanofiltration membrane 3 | 11 | 580 | 6.3 | 98.9 | 1721 | 320 | 81.4 | 10 | 5.4 | 54 | 97.7 |
| Example 70 | Nanofiltration membrane 4 | 9 | 589 | 7.1 | 98.8 | 1669 | 301 | 82.0 | 10 | 4.6 | 46 | 94.3 |
| Example 71 | Nanofiltration membrane 4 | 10 | 588 | 6.9 | 98.8 | 1701 | 309 | 81.8 | 10 | 4.6 | 46 | 94.4 |
| Example 72 | Nanofiltration membrane 4 | 11 | 580 | 7 | 98.8 | 1721 | 311 | 81.9 | 10 | 4.8 | 48 | 94.1 |

(3) Production of 1,5-Pentanediamine by the Transformant

The transformant was cultured as follows. To a test tube, 5 ml of MS medium shown in Table 6 was placed, and ampicillin was added to the medium to a final concentration of 50 mg/L, followed by inoculation of the CAD1 strain in an amount equivalent to that which can be picked up with a platinum loop. Pre-preculture was carried out at 30° C. for 24 hours by shaking.

TABLE 7

| Glucose | 50 | g/L |
|---|---|---|
| Magnesium sulfate heptahydrate | 1 | g/L |
| Ammonium sulfate | 16 | g/L |
| Potassium dihydrogen phosphate | 1 | g/L |
| Manganese (II) sulfate pentahydrate | 10 | mg/L |
| Iron (II) sulfate heptahydrate | 10 | mg/L |
| Yeast extract | 2 | g/L |

Subsequently, 95 ml of MS medium was placed in a 500 ml Erlenmeyer flask equipped with baffles, and ampicillin was added to the medium to a final concentration of 50 mg/L. To this medium, the total amount of the above culture was inoculated, followed by culture at 37° C. for 8 hours with stirring (preculture). This preculture was inoculated to a mini jar fermenter (manufactured by Biott Co., Ltd.; 2 L capacity) in which 1 L of MS medium was fed, and culture was carried out at a constant stirring rate (800 rpm), aeration rate (1 L/min.), temperature (37° C.) and pH (pH 6.5) (main culture). The pH was adjusted with 2 N sulfuric acid and 4 N sodium hydroxide, and 15 hours after the beginning of the culture, 100 mL of 50% glucose was added. The culture was terminated at 24 hours, and the concentration of 1,5-pentanediamine sulfate in the culture supernatant after removal of the bacterial cells was measured. The amount of its accumulation was confirmed to be 3 g/L.

Preparation of an Aqueous 1,5-Pentanediamine Sulfate Solution to be Subjected to Separation by the Nanofiltration Membrane To the culture supernatant containing 3 g/L 1,5-pentanediamine sulfate (50 L thereof was prepared by repeating fermentation) obtained by the fermentation method, 1 M aqueous calcium hydroxide solution (manufactured by Wako Pure Chemicals) was added to pH 9, 10 and 11, respectively, followed by stirring the resulting solution for 1 hour at 25° C. The precipitated calcium sulfate was filtered by suction filtration using qualitative filter paper No. 2 (manufactured by Advantec), thereby collecting 50 L of the filtrate.

Separation Experiment by the Nanofiltration Membrane

Subsequently, 50 L of the aqueous solution obtained as above was injected to the raw solution tank 1 of the membrane filtration device as shown in FIG. 1, and the pressure by the high-pressure pump 3 was adjusted to 1 MPa to allow the aqueous solution to pass through the nanofiltration membrane, thereby collecting the permeated solution 5. The concentrations of sulfate ion and calcium ion contained in the raw solution tank 1 and the permeated solution 5 were analyzed by an ion chromatography (manufactured by DIONEX), and the concentration of 1,5-pentanediamine was analyzed by a high-performance liquid chromatography (manufactured by Shimadzu Corporation). The results are shown in Table 8.

TABLE 8

| | | pH | Calcium ion concentration | | | Sulfate ion concentration | | | 1,5-Pentanediamine concentration | | | 1,5-Pentanediamine recovery (%) |
| | | | Raw solution (mg/L) | Permeated solution (mg/L) | Rejection rate (%) | Raw solution (mg/L) | Permeated solution (mg/L) | Rejection rate (%) | Raw solution (g/L) | Permeated solution (g/L) | Permeation rate (%) | |
|---|---|---|---|---|---|---|---|---|---|---|---|---|
| Example 73 | Nanofiltration membrane 1 | 9 | 601 | 0.9 | 99.9 | 1712 | 331 | 80.7 | 3 | 1.6 | 53 | 97.9 |
| Example 74 | Nanofiltration membrane 1 | 10 | 592 | 0.8 | 99.9 | 1711 | 314 | 81.6 | 3 | 1.7 | 57 | 99 |
| Example 75 | Nanofiltration membrane 1 | 11 | 599 | 0.7 | 99.9 | 1712 | 331 | 80.7 | 3 | 1.8 | 60 | 99.2 |
| Example 76 | Nanofiltration membrane 2 | 9 | 601 | 5.2 | 99.1 | 1712 | 351 | 79.5 | 3 | 1.5 | 50 | 97.5 |
| Example 77 | Nanofiltration membrane 2 | 10 | 592 | 5.3 | 99.1 | 1711 | 343 | 80.0 | 3 | 1.5 | 50 | 97.2 |
| Example 78 | Nanofiltration membrane 2 | 11 | 599 | 5.5 | 99.1 | 1712 | 331 | 80.7 | 3 | 1.6 | 53 | 97.4 |
| Example 79 | Nanofiltration membrane 3 | 9 | 601 | 5.7 | 99.1 | 1712 | 313 | 81.7 | 3 | 1.5 | 50 | 97.2 |
| Example 80 | Nanofiltration membrane 3 | 10 | 592 | 5.8 | 99.0 | 1711 | 320 | 81.3 | 3 | 1.4 | 47 | 97.3 |
| Example 81 | Nanofiltration membrane 3 | 11 | 599 | 5.9 | 99.0 | 1712 | 320 | 81.3 | 3 | 1.5 | 50 | 97.7 |
| Example 82 | Nanofiltration membrane 4 | 9 | 601 | 6.8 | 98.9 | 1712 | 315 | 81.6 | 3 | 1 | 33 | 93.9 |
| Example 83 | Nanofiltration membrane 4 | 10 | 592 | 6.9 | 98.8 | 1711 | 320 | 81.3 | 3 | 1.1 | 37 | 93.9 |
| Example 84 | Nanofiltration membrane 4 | 11 | 599 | 6.9 | 98.8 | 1712 | 317 | 81.5 | 3 | 1.1 | 37 | 94.1 |

As shown in Table 8, it can be seen that, by the nanofiltration membrane, calcium sulfate was removed at a high efficiency and 1,5-pentanediamine was recovered at a high yield at any of the pHs of 9, 10 and 11.

Example 85

Concentration and Distillation of the Aqueous 1,5-Pentanediamine Solution

Through a reverse osmosis membrane (reverse osmosis membrane: SU-810 manufactured by Toray Industries, Inc.), 48 L of the permeated solution (1,5-pentanediamine concentration: 8 g/L) separated by the nanofiltration membrane under the conditions in Example 13 was allowed to pass under an operation pressure of 3 MPa. The non-permeated solution of the reverse osmosis membrane was collected (80 g/L, 5 L), and water was evaporated under reduced pressure (50 hPa) using a rotary evaporator (manufactured by Tokyo Rikakikai), to concentrate the solution (950 g/L, 0.4 L). At this time, precipitation of calcium sulfate was not observed, and 1,5-pentanediamine could be recovered at a recovery of 99%.

Subsequently, distillation was carried out under a reduced pressure of 12 kPa at 100° C. Precipitation of calcium sulfate was not observed in the distillation residue, and distillation could be carried out at an yield of 99%.

Example 86

Production of a Polyamide

Fifty grams (100.8 mmol) of aqueous 50 wt % solution of the equimolar salt of the 1,5-pentanediamine obtained in Example 63 and adipic acid (manufactured by Wako Pure Chemicals) was prepared, and 1.542 g (1.512 mmol) of aqueous 10 wt % 1,5-pentanediamine solution was fed to the test tube, followed by placing the test tube in an autoclave, sealing the autoclave and replacing the atmosphere with nitrogen. The heater temperature was then set to 285° C., and heating was started. After attaining an internal pressure of 17.5 kg/cm$^2$, the internal pressure was maintained at 17.5 kg/cm$^2$ for 2 hours. Thereafter, the internal pressure was allowed to decrease to normal pressure over 1.5 hours, and when an internal temperature of 275° C. was attained, the heating was stopped. After allowing the reaction solution to cool to room temperature, the test tube was removed from the autoclave, to obtain a polypentamethylene adipamide resin.
Measurement of the Melting Point of the Polyamide Using a differential scanning calorimeter (Robot DSC RDC220 manufactured by SEIKO Electronic), 5 mg of a sample of the polyamide produced as above was taken and heated to 285° C., followed by maintaining the temperature for 3 minutes to completely melt the sample, cooling the sample to 30° C. at a rate of 20° C./min., maintaining the temperature for 3 minutes, and heating the sample from 30° C. to 285° C. at a rate of 20° C./min., under a nitrogen atmosphere. The temperature at which the endothermic peak (melting point) was observed was 254° C.
Measurement of the Viscosity of the Polyamide The relative viscosity ($\eta r$) of the polyamide produced as above was measured in 98% sulfuric acid at a concentration of 0.01 g/mL at 25° C. using an Ostwald viscometer, and found to be 2.76.

Comparative Example 1

Purification of 1,5-Pentanediamine Sulfate without Using a Nanofiltration Membrane In the same manner as in Example 13, 1 M aqueous calcium hydroxide solution was added to 10 g/L aqueous 1,5-pentanediamine sulfate solution (50 L) to pH 9, followed by stirring the resulting solution for 1 hour at 25° C. The precipitated calcium sulfate was filtered by suction filtration using qualitative filter paper No. 2 (manufactured by Advantec), thereby collecting 50 L of the filtrate. Subsequently, from 50 L of the filtrate, water was evaporated under reduced pressure (50 hPa) using a rotary evaporator (manufactured by Tokyo Rikakikai), to concentrate the solution (950 g/L, 0.4 L). At this time, precipitation of calcium sulfate was observed. Subsequent distillation under a reduced pressure of 12 kPa at 100° C. caused further precipitation of calcium sulfate in the distillation residue. The distillation yield was 70%.

Comparative Example 2

Purification of 1,5-Pentanediamine Adipate without Using a Nanofiltration Membrane In the same manner as in Example 39, 1 M aqueous calcium hydroxide solution was added to 10 g/L aqueous 1,5-pentanediamine adipate solution (50 L) to pH 11, followed by stirring the resulting solution for 1 hour at 25° C. The precipitated calcium sulfate was filtered by suction filtration using qualitative filter paper No. 2 (manufactured by Advantec), thereby collecting 50 L of the filtrate. Subsequently, from 50 L of the filtrate, water was evaporated under reduced pressure (50 hPa) using a rotary evaporator (manufactured by Tokyo Rikakikai), to concentrate the solution (950 g/L, 0.4 L). At this time, precipitation of calcium adipate was observed. Subsequent distillation under a reduced pressure of 12 kPa at 100° C. caused further precipitation of calcium sulfate in the distillation residue. The distillation yield was 30%.

Comparative Example 3

Purification of 1,5-Pentanediamine Sulfate by an Extraction Operation

In the same manner as in Example 13, 1 M aqueous calcium hydroxide solution was added to 10 g/L aqueous 1,5-pentanediamine sulfate solution (50 L) to pH 9, followed by stirring the resulting solution for 1 hour at 25° C. The precipitated calcium sulfate was filtered by suction filtration using qualitative filter paper No. 2 (manufactured by Advantec), thereby collecting 50 L of the filtrate. Subsequently, 20 L of chloroform (manufactured by Wako Pure Chemicals) was added to 50 L of the filtrate, and the resulting mixture was subjected to extraction with a separatory funnel. Using HPLC, 1,5-pentanediamine contained in each of the extracted organic layer and aqueous layer was analyzed, and the recovery into the organic layer was found to be 50%. To the aqueous layer after the extraction, 20 L of chloroform was added, and the extraction was repeated with the separatory funnel. However, the recovery never exceeded 80%. Further, not less than 100 L of organic solvent waste was produced by the extraction operation.

From the results in the above Examples and Comparative Examples, it was revealed that a diamine can be recovered at a high yield by removing a diamine salt highly efficiently from an aqueous solution containing the salt by the nanofiltration membrane, and that the diamine can be used as a raw material for a polyamide. That is, it was revealed that, by filtering an aqueous solution containing a diamine salt using the nanofiltration membrane, a diamine as a raw material for a polyamide can be purified at a higher yield than by an extraction operation using an organic solvent.

INDUSTRIAL APPLICABILITY

Since, by the method for producing a diamine, a salt contained in an aqueous diamine salt solution can be removed effectively by a simpler operation than a conventional extraction operation with an organic solvent, the method is useful in cases where a diamine suitable as a raw material for a polyamide is to be obtained.

The invention claimed is:

1. A method for producing a diamine comprising purifying a diamine from an aqueous solution containing a diamine salt by adding an alkaline substance to the aqueous solution and then filtering the resulting solution by allowing the solution to pass through a nanofiltration membrane to remove the salt, thereby obtaining an aqueous diamine solution.

2. The method according to claim 1, wherein said diamine salt is a salt of a diamine represented by Chemical Formula (1):

$$H_2N-(CH_2)_n-NH_2 \qquad (1)$$

wherein n represents an integer of 1 to 10.

3. The method according to claim 1, wherein said diamine salt is a diamine inorganic acid salt or a diamine dicarboxylate.

4. The method according to claim 1, wherein said alkaline substance is sodium hydroxide, potassium hydroxide, calcium hydroxide or ammonia.

5. The method according to claim 1, wherein a functional layer of said nanofiltration membrane comprises a polyamide.

6. The method according to claim 5, wherein said polyamide comprises a cross-linked piperazine polyamide as a major component and a constituting component represented by Chemical Formula (2):

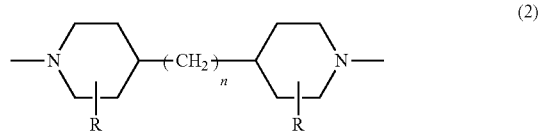

wherein R represents —H or —CH$_3$, and n represents an integer of 0 to 3.

7. The method according to claim 1, wherein the aqueous solution after the addition of an alkaline substance has a pH of not less than 9 and not more than 12.

8. The method according to claim 1, wherein filtration pressure of said aqueous solution is not less than 0.1 MPa and not more than 8 MPa.

9. The method according to claim 1, wherein said aqueous diamine solution obtained is further subjected to distillation under a pressure of not less than 1 Pa and not more than atmospheric pressure, at a temperature of not less than 25° C. and not more than 200° C.

10. The method according to claim 1, wherein said aqueous diamine solution obtained is further subjected to a step of filtering through a reverse osmosis membrane to increase the diamine concentration.

11. A method for producing a polyamide comprising polycondensation of said diamine obtained by the method according to claim 1 with a dicarboxylic acid.

12. The method according to claim 11, wherein said dicarboxylic acid is adipic acid.

13. The method according to claim 2, wherein said diamine salt is a diamine inorganic acid salt or a diamine dicarboxylate.

14. The method according to claim 2, wherein said alkaline substance is sodium hydroxide, potassium hydroxide, calcium hydroxide or ammonia.

15. The method according to claim 3, wherein said alkaline substance is sodium hydroxide, potassium hydroxide, calcium hydroxide or ammonia.

16. The method according to claim 2, wherein a functional layer of said nanofiltration membrane comprises a polyamide.

17. The method according to claim 3, wherein a functional layer of said nanofiltration membrane comprises a polyamide.

18. The method according to claim 4, wherein a functional layer of said nanofiltration membrane comprises a polyamide.

19. The method according to claim 2, wherein the aqueous solution after the addition of an alkaline substance has a pH of not less than 9 and not more than 12.

20. The method according to claim 3, wherein the aqueous solution after the addition of an alkaline substance has a pH of not less than 9 and not more than 12.

* * * * *